United States Patent
Xie et al.

(10) Patent No.: US 10,930,031 B2
(45) Date of Patent: Feb. 23, 2021

(54) SYNCHRONIZATION METHOD AND SYSTEM FOR SINGLE EVENT LIST TYPE DATA IN PET IMAGING

(75) Inventors: Qingguo Xie, Suzhou (CN); Yuanbao Chen, Suzhou (CN); Jun Zhu, Suzhou (CN); Xin Chen, Suzhou (CN); Zhongyi Wu, Suzhou (CN); Luyao Wang, Suzhou (CN)

(73) Assignee: RAYCAN TECHNOLOGY CO., LTD. (SU ZHOU), Suzhou (CN)

( * ) Notice: Subject to any disclaimer, the term of this patent is extended or adjusted under 35 U.S.C. 154(b) by 982 days.

(21) Appl. No.: 14/408,935

(22) PCT Filed: Aug. 14, 2012

(86) PCT No.: PCT/CN2012/080095
§ 371 (c)(1),
(2), (4) Date: Dec. 17, 2014

(87) PCT Pub. No.: WO2014/005366
PCT Pub. Date: Jan. 9, 2014

(65) Prior Publication Data
US 2015/0302614 A1    Oct. 22, 2015

(30) Foreign Application Priority Data
Jul. 2, 2012 (CN) .......................... 201210222177.7

(51) Int. Cl.
*G06T 11/00* (2006.01)
*G01T 1/29* (2006.01)
*A61B 6/03* (2006.01)

(52) U.S. Cl.
CPC ............ *G06T 11/006* (2013.01); *A61B 6/037* (2013.01); *G01T 1/2985* (2013.01)

(58) Field of Classification Search
CPC ...... G01T 1/2985; G06T 11/006; A61B 6/037
(Continued)

(56) References Cited

U.S. PATENT DOCUMENTS 5,272,344 A    12/1993  Williams
2006/0102845 A1*  5/2006  Williams ................ G01T 1/172
                                                      250/363.03
(Continued)

FOREIGN PATENT DOCUMENTS

CN    101088028 A    12/2007
CN    101268949 A     9/2008
(Continued)

OTHER PUBLICATIONS

1st Japanese Office Action in JP Application No. 2015-518777 dated Jan. 5, 2016 in 6 pages.
(Continued)

*Primary Examiner* — Yoshihisa Ishizuka
(74) *Attorney, Agent, or Firm* — Knobbe, Martens, Olson & Bear, LLP

(57) ABSTRACT

A method for synchronizing list-mode data of single events in a PET imaging includes: acquiring list-mode data of single events of each independent detector module, calculating a probability density of time intervals between occurrences of single events in detector module and setting initial parameters, determining detection starting time difference of each detector module with iterative peak searching and graded time window, and performing synchronization correction and coincidence discrimination on the single event data in each detector module based on the detection starting time difference. A system for synchronizing list-mode data of single events in a PET imaging includes: a data acquisition and frequency difference compensation module, an initial parameter setting module, a coarse time scale coincidence module, a fine time scale coincidence module and a data synchronization correction and coincidence discrimination module.

15 Claims, 6 Drawing Sheets

(58) Field of Classification Search
USPC .......................................................... 702/181
See application file for complete search history.

(56) References Cited

U.S. PATENT DOCUMENTS

| | | | | |
|---|---|---|---|---|
| 2007/0131857 | A1* | 6/2007 | Thompson | G01T 1/2985 |
| | | | | 250/252.1 |
| 2009/0072152 | A1 | 3/2009 | Chen et al. | |
| 2009/0114826 | A1* | 5/2009 | Takahashi | G01T 1/249 |
| | | | | 250/363.03 |
| 2009/0309031 | A1* | 12/2009 | Ohtani | G01T 1/2985 |
| | | | | 250/363.03 |
| 2011/0079722 | A1 | 4/2011 | Gagnon | |
| 2011/0163238 | A1* | 7/2011 | Teshigawara | G01T 1/40 |
| | | | | 250/363.03 |
| 2011/0240864 | A1* | 10/2011 | Degenhardt | G01T 1/00 |
| | | | | 250/362 |
| 2011/0278466 | A1 | 11/2011 | Frach et al. | |
| 2012/0068077 | A1* | 3/2012 | Frach | A61B 6/037 |
| | | | | 250/369 |
| 2012/0153165 | A1 | 6/2012 | Ott | |
| 2012/0228511 | A1* | 9/2012 | Moteki | G01T 1/1647 |
| | | | | 250/363.03 |

FOREIGN PATENT DOCUMENTS

| | | |
|---|---|---|
| CN | 102151142 A | 8/2011 |
| CN | 102274041 A | 12/2011 |
| EP | 2341370 A2 | 7/2011 |
| JP | H07-503077 A | 3/1995 |
| JP | 2008-107326 A | 5/2008 |
| JP | 2008-538606 A | 10/2008 |
| JP | 2010-217096 A | 9/2010 |
| JP | 2011-141139 A | 7/2011 |
| JP | 2011-520119 A | 7/2011 |
| JP | 2011-232044 A | 11/2011 |
| JP | 2012-511717 A | 5/2012 |
| WO | 2011/121737 A1 | 10/2011 |

OTHER PUBLICATIONS

Extended European Search Report in EP Application No. 12880398 dated Jan. 28, 2016 in 6 pages.

Kim, Ealgoo et al., "Optical Network-based PET DAQ System: One Fiber Optical Connection," IEEE Nuclear Science Symposium, Sep. 2010, p. 2020-2025.

Nang, Chao et al., "A Real Time Coincidence System for High Count-Rate TOF or Non-TOF PET Cameras Using Hybrid Method Combining AND-Logic and Time-Mark Technology," IEEE Transactions on Nuclear Science, vol. 57, No. 2, Apr. 2010, p. 708-714.

International Search Report dated Apr. 18, 2013 of PCT/CN2012/080095 which is the parent application—5 pages.

McElroy et al., "A true singles list-mode data acquisition system for a small animal PET scanner with independent crystal readout", Physics in Medicine and Biology, 2005, vol. 50, pp. 3323-3335.

Cherry et al., " PET: Physics, Instrumentation, and Scanners", Springer New York, 2004 in 135 pages.

Tetrault et al.,"Real Time Coincidence Detection Engine for High Count Rate Timestamp Based PET", IEEE Transactions on Nuclear Science, Feb. 2010, vol. 57, No. 1, pp. 117-124.

Xie et al., "A Simple All-digital PET System", Proc. of SPIE vol. 6510 in 9 pages.

McElroy et al., "Use of a Central Positron Emitting Reference Source to Improve the Timing Alignment of a Singles List-Mode Small Animal PET Scanner", IEEE Transactions on Nuclear Science, Feb. 2007, vol. 54, No. 1, pp. 50-54.

* cited by examiner

SYNCHRONIZATION METHOD AND SYSTEM FOR SINGLE EVENT LIST TYPE DATA IN PET IMAGING

This application is the national phase of International Application No. PCT/CN2012/080095, titled "METHOD FOR SYNCHRONIZING LIST-MODE DATA OF SINGLE EVENTS IN PET IMAGING AND SYSTEM THEREOF", filed on Aug. 14, 2012, which claims the priority to Chinese Patent Application No. 201210222177.7, entitled "METHOD FOR SYNCHRONIZING LIST-MODE DATA OF SINGLE EVENTS IN PET IMAGING AND SYSTEM THEREOF", filed with the State Intellectual Property Office of the People's Republic of China on Jul. 2, 2012, which are incorporated by reference in their entireties herein.

FIELD OF THE TECHNOLOGY

The present disclosure relates to radiation detection imaging technologies, and particularly, to a method for synchronizing list-mode data of single events in a Positron Emission Tomography and a system thereof.

BACKGROUND

Positron Emission Tomography (PET) is a non-invasive radiography method. The fundamental principle of the PET imaging is given as follows. A positron radionuclide is labeled on a molecular probe. After a positron generated due to a decay of the radionuclide gets in collision with a negatron in vivo then the positron and the negatron annihilate each other, two γ photons having an energy of 511 keV are emitted in almost opposite directions. In the PET, sensitive radiation detectors that surround an object are used to convert incident γ photons into an electrical signal, thereby obtaining energy information, position information and time information of the γ photons. A position on a line-of-response where an annihilation event locates is obtained by the annihilation coincidence technology, and distribution of the positron nuclides in vivo is obtained by a 2-dimensional or a 3-dimensional tomographic reconstruction algorithm; hence, the physiological and biochemical processes in vivo are observed in vitro [Michael E. Phelps, PET Physics, Instrument, and Scanners, Springer, 2006].

Coincidence detection is a key link of the PET imaging. Currently, approaches for implementing the coincidence detection are mainly based on timestamp and AND-gate. Compared with the AND-gate based coincidence detection approach, the timestamp based coincidence detection approach is more widespread because of advantages of timeliness, scalability and adaptability [M.-A. Tetrault, J. Oliver, M. Bergeron, R. Lecomte and R. Fontaine, "Real Time coincidence detection engine for high count rate timestamp based PET", IEEE Trans. Nucl. Sci, vol. 57, no. 1, pp. 117-124, February, 2010]. However, for the timestamp based coincidence detection approach, time synchronization is a very important issue, since the precision and stability of time synchronization have a direct influence on a system-level time resolution. With a good time resolution, a smaller time window may be set and more random events may be excluded, thereby obtaining a better Noise Equivalent Count Rate (NECR), and improving imaging quality and Signal to Noise Ratio.

In a conventional PET system, generally, all data acquisition boards are connected onto a backplane, and clock synchronization is achieved with a clock distribution network on the backplane. In this way, small clock skew and clock jitter can be achieved. However, usually the backplane is tightly bound to a detector structure and a hardware coincidence circuit; hence, the flexibility, maintainability and scalability of the system are severely constrained [D. P. McElroy, M. Hoose, W. Pimpl, V. Spanoudaki, T. Schuler, and S. I. Ziefler, "A true singles list-mode data acquisition system for a small animal PET scanner with independent crystal readout", Phys. Med. Biol. Vol. 50, pp. 3323-3335, 2005]. In recent years, as a software coincidence detection approach based on list-mode data of single events gets widely used in the PET imaging. And multiple time synchronization methods are disclosed successively. For example, in a global clock method, time synchronization is achieved by transferring a high-precision reference clock source and a synchronization signal to respective data acquisition boards through cables. However due to the usage of cables in this method, the clock synchronization signal is inevitably affected by factors such as delay, decay and noise; hence, time correction is needed to be periodically performed. For another example, in a synchronous ethernet method, good synchronization is achieved using an ethernet transmission medium and a precision time protocol. However, in this method, extra requirements are set for the hardware, thereby increasing the cost of system design.

Accordingly, in view of the technical problems described above, a method for synchronizing list-mode data of single events in a PET imaging and a system thereof, with an improved structure, are needed to overcome the above flaws.

SUMMARY

In view of this, a method for synchronizing list-mode data of single events in a PET imaging and a system thereof are provided in the disclosure, to perform a time synchronous correction on acquired list-mode data of the single events in a PET imaging under conditions that each basic detector module works with a local reference clock source and no hardware synchronization signal is provided. With the method, the list-mode data of the single events may be effectively and accurately synchronized, a coincidence event may be extracted accurately. Besides, the complexity of hardware design of the system is significantly reduced, and the flexibility, scalability and maintainability of the system are improved.

Accordingly, a technical solution is provided in the disclosure as follows.

A method for synchronizing list-mode data of single events in a PET imaging, includes:

step 1, acquiring and storing, by a computer, list-mode data of single events of each of a plurality of basic detector modules working with a local reference clock source, and performing, by a receiving device, a frequency difference compensation on the list-mode data of the single events based on a time difference between two synchronization requests of each of the plurality of basic detector modules;

step 2, calculating, by the computer, a probability density of time intervals between occurrences of single events in a single event data set acquired by each of the plurality of basic detector modules, and setting, by the computer, initial parameters comprising an initial iteration space parameter $TR_{ini}$, an initial time interval parameter $\Delta T_{ini}$ and an initial time window parameter $TW_{ini}$;

step 3, performing, by the computer, based on the initial parameters set in the step 2 and with an iterative peak searching, a synchronization correction and a coincidence peak searching on the single event data set acquired by each of the plurality of basic detector modules; and determining, by the computer, a coarse estimated value of a detection starting time difference of each of the plurality of basic detector modules, wherein, the synchronization correction comprises adjusting, based on the time interval parameter calculated by each of the plurality of basic detector modules, time instants at which the single events occur in each of the plurality of basic detector modules, and the coincidence peak searching is performed based on a statistical characteristic of events in the PET imaging, a statistical characteristic of the coincidence events is a Gaussian distribution, and a statistical characteristic of random events is a uniform random distribution;

step 4, performing, by the computer, based on the coarse estimated value of detection starting time difference obtained in the step 3 and with a graded time window, the synchronization correction and the coincidence peak searching on the single event data set acquired by each of the plurality of basic detector modules; and determining a fine estimated value of the detection starting time difference of each of the plurality of basic detector modules;

step 5, performing, by the computer, a weight accumulation on the coarse estimated value and the fine estimated value of the detection starting time difference, respectively obtained in the step 3 and the step 4, to determine the detection starting time difference of each of the plurality of basic detector modules; and performing, by the computer, the synchronization correction and a coincidence event discrimination on the single event data set acquired by each of the plurality of basic detector modules, to obtain coincidence events; and step 6, forming, by the computer, an image based on the coincidence events.

Preferably, in the step 1, each of the plurality of basic detector modules generates the list-mode data of the single events comprising time information, energy information and position information of the events, and the list-mode data of the single events are transferred to and stored in a computer.

Preferably, wherein the frequency difference compensation in the step 1 comprises: periodically sending, by each of the plurality of basic detector modules, frequency synchronization requests in a data transmission channel based on a value of a counter in each of the plurality of basic detector modules;

measuring, by a receiving device, a time difference between two synchronization requests of each of the plurality of basic detector modules; and generating, by the computer, a look-up table for frequency differences of each of the plurality of basic detector modules based on the respective time differences, to compensate, in real time, the frequency differences introduced by the local reference clock source.

Preferably, in the step 2, a probability density $f_i(x)$ of time intervals $TI_i$ between the occurrences of the single events in the single event data set acquired by each of the plurality of basic detector modules is obtained by, performing a backward difference on each single event data set and performing a statistical analysis on obtained differential data, where i represents serial numbers of each of the plurality of basic detector modules and x represents the time intervals of the occurrences of the single events.

Preferably, in the step 2, the initial parameters are set performing calculations on the probability density of the time intervals between the occurrences of the single events in the single event data set acquired by each of the plurality of basic detector modules, and setting, by the computer, the initial parameters comprises:

step 2.1 of initializing the iteration space parameter $TR_{ini}$, comprising:

performing a merge sort on the single event data sets of each of the plurality of basic detector modules; searching for a position M corresponding to a detection starting time instant $T_i$ of an i-th basic detector module in an obtained list; reading an instant event time $T_{ci}$ corresponding to a position M-N in the list, where N is the number of consecutive events from an identical basic detector module, $N \in [1, M-1]$; and calculating a probability of an occurrence of $T_{ci}$ with a formula of:

$$P_i < \int_{T_i-T_{ci}}^{+\infty} f_k(x)dx \cdot \int_{(T_i-T_{ci})/N}^{+\infty} f_i(x)dx;$$

wherein k is a serial number of a basic detector module corresponding to a position 1 in the obtained list, and an initial value $TR_{ini}$ of the iteration space parameter is determined with a formula of:

$$TR_{ini} = T_i - T_{ci};$$

where $T_{ci}$ is the instant event time corresponding to the position M-N in the obtained list;

step 2.2 of initializing the time interval parameter $\Delta T_{ini}$, comprising:

reading an instant event time $T_k$ corresponding to the position 1 in the list obtained in the step 2.1, and determining an initial value $\Delta T_{ini}$ of a difference between detection starting time instants of the i-th basic detector module and the k-th basic detector module with a formula of:

$$\Delta T_{ini} = T_i - T_k + TR_{ini}/2 \quad i \neq k,$$
$$\Delta T_{ini} = 0 \quad i = k;$$

step 2.3 of initializing the time window parameter $TW_{ini}$, comprising:

reading the instant event time $T_k$ corresponding to the position 1 in the list obtained in the step 2.1, and determining an initial value $TW_{ini}$ of a coincidence time window of the i-th and the k-th basic detector modules with a formula of:

$$TW_{ini} = TR_{ini}/L_i;$$

where $L_i$ represents coefficient factors of time windows of each of the plurality of basic detector modules, and $L_i$ is determined with a formula of:

$$L_i > 2 \cdot \frac{TR_{ini}}{E(TI_i) + E(TI_k)};$$

where $E(TI_k)$ is an expectation of time intervals of occurrences of events of each of the plurality of basic detector modules k which transfers single event data first, and $E(TI_i)$ is an expectation of time intervals of occurrences of events of each of the plurality of basic detector modules i requiring synchronization and is determined with a formula of:

$$E(TI_i) = \int_{-\infty}^{+\infty} x \cdot f_i(x) dx.$$

Preferably, in the step 3, the coarse estimated value $\Delta T_{crs}$ of the detection starting time difference of each of the plurality of basic detector modules is determined through a coarse time scale coincidence, and the step 3 comprises:

step 3.1, performing, based on the initial parameters set in the step 2, the synchronization correction and the coincidence peak searching on the single event data set acquired by each of the plurality of basic detector modules;

step 3.2, analyzing a coincidence result obtained in the step 3.1; in the case that a peak in a statistical histogram of coincidence events is obtained, stopping an iteration; otherwise, adjusting the time interval parameter $\Delta T_{ini}$ to perform the coincidence peak searching and repeating the step 3.2; and step 3.3, setting, based on a center offset $\Delta T_{offset}$ of the statistical histogram of the coincidence events obtained in the step 3.2, the coarse estimated value $\Delta T_{crs}$ of the detection starting time difference of each of the plurality of basic detector modules.

Preferably, in the step 4, the fine estimated value $\Delta T_{fine}$ of the detection starting time difference of each of the plurality of basic detector modules is determined with a fine time scale coincidence, and the step 4 comprises:

step 4.1, performing, based on the coarse estimated value $\Delta T_{crs}$ of the detection starting time difference of each of the plurality of basic detector modules obtained in the step 3.2, the synchronization correction, and a coincidence peak searching with the initial time window $TW_{ini}$ on the single event data set in each of the plurality of basic detector modules;

step 4.2, analyzing a center offset $\Delta T_i$ of an obtained statistical histogram of coincidence events; in the case that the center offset $\Delta T_i$ meets a precision index requirement, stop the iteration; otherwise, performing the coincidence peak searching with a graded time window and repeating the step 4.2; and step 4.3, performing a weight accumulation on the obtained center offset $DT_i$, to obtain the fine estimated value $\Delta T_{fine}$, where i is the number of iteration.

Preferably, in the step 4.2, setting the graded time window comprises: setting coincidence time windows with various sizes, to gradually approximate a precision of the obtained statistical histogram of the coincidence events to a precision index.

Preferably, the precision index is a precision of a resolution of coincidence time.

According to another aspect of the present disclosure, a system for synchronizing list-mode data of single events in a PET imaging is provided. The system includes a data acquisition and frequency compensation module, an initial parameter setting module 200, a coarse time scale coincidence module 300, a fine time scale coincidence module 400, and a data synchronization correction and coincidence discrimination module 500; wherein the data acquisition and frequency compensation module 100 is configured to, acquire and store list-mode data of single events of each of a plurality of basic detector modules working with respective local reference clock sources, and perform a frequency difference compensation on the list-mode data of the single events based on a time difference between two synchronization requests of each of the plurality of basic detector modules;

the initial parameter setting module 200 is configured to, calculate a probability density of time intervals between occurrences of single events in a single event data set acquired by each of the plurality of basic detector modules, and set initial parameters comprising an initial iteration space parameter $TR_{ini}$, an initial time interval parameter $\Delta T_{ini}$ and an initial time window parameter $TW_{ini}$;

the coarse time scale coincidence module 300 is configured to, obtain a coarse estimated value of a detection starting time difference of each of the plurality of basic detector modules;

the fine time scale coincidence module 400 is configured to, obtain a fine estimated value of the detection starting time difference of each of the plurality of basic detector modules; and the data synchronization correction and coincidence discrimination module 500 is configured to, determine the detection starting time difference of each of the plurality of basic detector modules, and perform a synchronization correction and a coincidence event discrimination on each single event data set, to obtain coincidence events, wherein, the synchronization correction comprises adjusting, based on the time interval parameter calculated by each of the plurality of basic detector modules, time instants at which the single events occur in each of the plurality of basic detector modules, and the coincidence peak searching is performed based on a statistical characteristic of events in the PET imaging, a statistical characteristic of the coincidence events is a Gaussian distribution, and a statistical characteristic of random events is a uniform random distribution, and wherein, an image is formed based on the coincidence events.

Preferably, the data acquisition and frequency compensation module 100 comprises a data acquisition module 110 and a frequency compensation module 120, the data acquisition module 110 is configured to, transfer the list-mode data of the single events comprising time information, energy information and position information of the single events, generated by each of the plurality of basic detector modules and sorted chronologically, to a computer, and store the list-mode data in the computer; and the frequency compensation module 120 is configured to, compensate frequency differences of the local reference clock sources used in each of the plurality of basic detector modules, and transfer the compensated list-mode data of the single events to the initial parameter setting module 200.

Preferably, the initial parameter setting module 200 comprises a single event occurrence time interval probability density calculation module 210 and an initial iteration parameter setting module 220, the single event occurrence time interval probability density calculation module 210 is configured to, calculate the probability density of the time intervals between the occurrences of the single events in the single event data set in each of the plurality of basic detector modules; and the initial iteration parameter setting module 220 is configured to, set the initial parameters, and transfer the initial parameters to the coarse time scale coincidence module 300 and the fine time scale coincidence module 400.

Preferably, the single event occurrence time interval probability density calculation module 210 performs a backward difference on the single event data set in each of the plurality of basic detector modules and performs a statistical analysis on obtained differential data.

Preferably, the coarse time scale coincidence module 300 performs, based on the initial parameters set by the initial parameter setting module 200 and with an iterative peak searching, the synchronization correction and a coincidence peak searching on the single event set acquired by each of the plurality of basic detector modules, to obtain the coarse estimated value of the detection starting time difference of each of the plurality of basic detector modules; wherein the coincidence peak searching is performed base on a statistical characteristic of events in the PET imaging.

Preferably, the fine time scale coincidence module 400 performs, based on the coarse estimated value obtained by the coarse time scale coincidence module 300 and with a graded time window, the synchronization correction and a coincidence peak searching on the single event data set obtained by each of the plurality of basic detector modules, to determine the fine estimated value of the detection starting time difference of each of the plurality of basic detector modules; wherein setting the graded time window comprises setting coincidence time windows with various sizes, to gradually approximate a precision of the obtained statistical histogram of the coincidence events to a precision index.

According to the foregoing technical solutions, with the method for synchronizing the list-mode data of the single events in the PET imaging and the system thereof in the embodiments of the disclosure, without a global reference clock source realized by extra hardware or a synchronization signal, the list-mode data of the single events may be synchronized effectively and accurately, coincidence events may be extracted accurately, and a rapid module-level time correction may be achieved. Furthermore, with the disclosure, the complexity of hardware design is significantly reduced, the construction cost is lowered, and the flexibility, scalability and maintainability of the system are improved.

BRIEF DESCRIPTION OF THE DRAWINGS

To interpret technical solutions of embodiments of the present disclosure or conventional technical solutions better, drawings to be used for the embodiments and for the description of conventional technical solutions are described briefly. Apparently, the drawings described below are merely a part of embodiments of the disclosure. For one skilled in the art, other drawings may be obtained based on these drawings without any creative work.

FIG. 1 shows an affect on coincidence event discrimination by adopting a synchronization signal in a method for synchronizing list-mode data of single events in a PET imaging provided in the disclosure, where

FIG. 5 illustrates statistical distribution charts of coincidence events, obtained through a fine time scale coincidence in the disclosure; where

FIG. 7 shows an affect on a coincidence time resolution with the disclosure, where

DETAILED DESCRIPTION OF THE EMBODIMENTS

A method for synchronizing list-mode data of single events in PET imaging and a system thereof are provided in the disclosure, to perform a time synchronous correction on acquired list-mode data of the single events in a PET imaging under conditions that each basic detector module works with a local reference clock source and no hardware synchronization signal is provided. With the method, the list-mode data of the single events may be effectively and accurately synchronized, a coincidence event may be extracted accurately, the complexity of hardware design of the system is significantly reduced, and the flexibility, scalability and maintainability of the system are improved.

Technical solutions according to the embodiments of the disclosure are clearly and completely described hereinafter in conjunction with drawings in the embodiments of the disclosure. It is apparent that the described embodiments are merely a part of the embodiments of the disclosure, rather than all the embodiments. Based on the embodiments of the disclosure, all other embodiments obtained by those skilled in the art without creative work are within the scope of protection of the disclosure.

Figure 2:
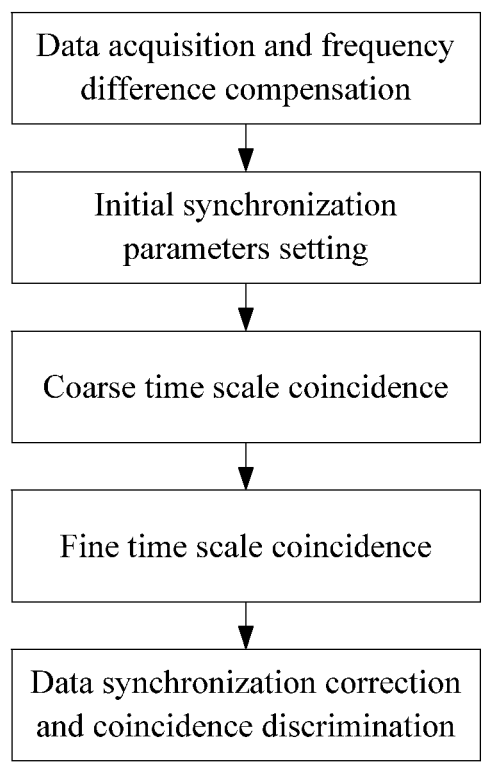
FIG. 2 is a flow chart of a method for synchronizing list-mode data of single events in a PET imaging provided in the disclosure.

As shown in FIG. 2, a method for synchronizing list-mode data of single events in PET imaging provided in the disclosure includes the following steps (1)-(5).

In the step (1), list-mode data of single events, generated by respective detector modules working with a local reference clock source, is acquired and stored; and a frequency difference compensation is respectively performed on the data of the single events. The step (1) includes a step (1.1) and a step (1.2).

In the step (1.1), the list-mode data of the single events including time information, energy information and position information of the single events, generated by the respective detector modules working with the local reference clock source, is transferred to and stored in a computer.

In the step (1.2), the acquired list-mode data of the single events is sorted by timestamps, and a corresponding frequency difference compensation is performed.

The frequency difference compensation in the step (1.2) may be implemented in many ways. For example, each detector module may periodically send frequency synchronization requests in a data transmission channel based on a value of a counter in the detector module; a receiving device measures a time difference between two synchronization requests of each detector module; and a look-up table for frequency differences of the detector modules is generated based on the respective time differences, to compensate, in real time, the frequency differences introduced by the local reference clock source.

In the step (2), a probability density of time intervals between occurrences of single events in a single event data set acquired by each detector module is calculated, and initial parameters including initial iteration space parameter $TR_{ini}$, initial time interval parameter $\Delta T_{ini}$ and initial time window parameter $TW_{ini}$ are set. These initial parameters are set based on a calculation of the probability density of the time intervals between the occurrences of the single events in the single event data set acquired by each detector module. Setting of the initial parameters includes the following steps (2.1)-(2.4).

Figure 3:
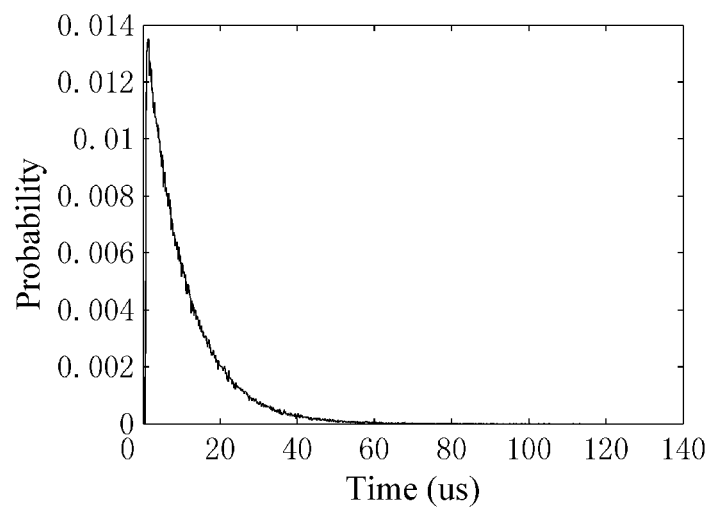
FIG. 3 illustrates a spectrum of a probability density of time intervals between occurrences of single events in a single event data set acquired by a basic detector module.

In the step (2.1), a backward difference is performed on respective single event data sets processed in the step (1.2), to obtain a statistical distribution of time intervals $TI_i$ between the occurrences of the single events in the single event data set obtained by each detector module, and a probability density function $f_i(x)$ of the time intervals between the occurrences of the single events is further obtained, where i represents serial numbers of the detector modules, and x represents the time intervals between the occurrences of the single events, as illustrated in FIG. 3.

In the step (2.2), the initial iteration space parameter $TR_{ini}$ is set based on the probability density, obtained in the step (2.1), of the time intervals between the occurrences of the single events in the single event data set acquired by each detector module. This step is detailed as follows.

A merge sort is performed on the single event data sets of the respective detector modules; a position M corresponding to a detection starting time instant $T_i$ of an i-th detector module is searched for in an obtained list; an instant event time $T_{ci}$ corresponding to a position M-N in the list is read, where N is the number of consecutive events from an identical detector module, $N \in [1, M-1]$; and a probability of an occurrence of $T_{ci}$ is calculated with the following formula:

$$P_i < \int_{T_i - T_{ci}}^{+\infty} f_k(x) dx \cdot \int_{\frac{(T_i - T_{ci})}{N}}^{+\infty} f_i(x) dx.$$

Where k is the serial number of a detector module corresponding to a position 1 in the obtained list. In the case that $P_i$ is small enough (for example, $P_i \ll 1e^{-7}$), it is impossible for N consecutive events from an identical detector module to occur. Hence, the initial iteration space parameter $TR_{ini}$ may be determined with the following formula:

$$TR_{ini} = T_i - T_{ci},$$

where $T_{ci}$ is the instant event timeinstant event time corresponding to the position M-N in the obtained list.

In the step (2.3), an initial value of the initial time interval parameter $\Delta T_{ini}$ is set with the following processes:

Reading an instant event time $T_k$ corresponding to the position 1 in the list obtained in step (2.2), and determining the initial value $\Delta T_{ini}$ of a difference between respective detection starting time instants of the i-th detector module and the k-th detector module with the following formula:

$$\Delta T_{ini} = T_i - T_k + \frac{TR_{ini}}{2} \quad i \neq k$$
$$\Delta T_{ini} = 0 \quad i = k$$

In the step (2.4), an initial value of the initial time window parameter $TW_{ini}$ is set with the following processes:

reading the instant event time $T_k$ corresponding to the position 1 in the list obtained in step (2.2), and determining an initial coincidence time window $TW_{ini}$ of the i-th and the k-th detector modules with the following formula:

$$TW_{ini} = TR_{ini}/L_i.$$

Where $L_i$ represents coefficient factors of time windows of the respective detector modules, and may be determined with the following formula:

$$L_i > 2 \cdot \frac{TR_{ini}}{E(TI_i) + E(TI_k)}.$$

Where $E(TI_k)$ is an expectation of time intervals of occurrences of events of the detector module k which transfers the single event data first; $E(TI_i)$ is an expectation of time intervals of occurrences of events of the detector module i requiring synchronization, And $E(TI_i)$ may be determined with the following formula:

$$E(TI_i) = \int_{-\infty}^{+\infty} x \cdot f_i(x) dx.$$

In the step (3), a synchronization correction and a coincidence peak searching are performed, based on the parameters set in the step (2) and with an iterative peak searching, on the single event data sets acquired by the respective detector modules, And a coarse estimated value $\Delta T_{crs}$ of a detection starting time difference of each detector module is obtained through a coarse time scale coincidence. The step (3) includes steps (3.1), (3.2) and (3.3).

In the step (3.1), the synchronization correction and the coincidence peak searching are performed on the respective single event data sets based on initial iteration parameters set in the step (2).

Figure 4:
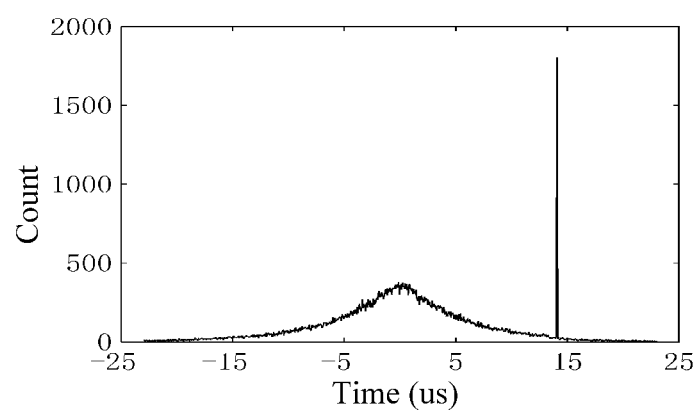
FIG. 4 is a statistical distribution chart of coincidence events, obtained through a coarse time scale coincidence in the disclosure.

In the step (3.2), a coincidence result obtained in the step (3.1) is analyzed. For each detector module, in case that a peak in a statistical histogram of coincidence events, as shown in FIG. 4, may be obtained. Then an iteration is stopped, and a center offset $\Delta T_{offset}$ of the histogram of the coincidence events is set as the coarse estimated value $\Delta T_{crs}$ of the detection starting time difference of the detector module. Otherwise, the time interval parameter $\Delta T_{ini}$ is adjusted by taking $TW_{ini}$ as a step size, and a peak of the histogram of the coincidence events is further searched for in a range of $TR_{ini}$. In the case that a peak of the histogram of the coincidence events is found, here an iteration number N and a time offset $\Delta T_{offset}$ corresponding to the peak in the histogram of the coincidence events are recorded; in case that a peak of the histogram of the coincidence events is still not found in the range of $TR_{ini}$, the value of $TR_{ini}$ is increased and a peak of the histogram of the coincidence events is further searched for.

In the step (3.3), based on the step (3.2), the coarse estimated value $\Delta T_{crs}$ of the detection starting time difference of each detector module may be determined with the following formula:

$$\Delta T_{crs} = \Delta T_{ini} + (N-1) \times TW_{ini} + \Delta T_{offset}.$$

Where, the synchronization correction in the step (3.1) is adjusting, based on the time interval parameter calculated by each detector module, time instants at which the single events occur in each detector module. The coincidence peak searching in the step (3.1) is performed based on a statistical characteristic of the events in the PET imaging, i.e., the statistical characteristic of the coincidence events is a Gaussian distribution, and the statistical characteristic of random events is a uniform random distribution.

In the step (4), the synchronization correction and the coincidence peak searching are performed, based on differences of coarse time $\Delta T_{crs}$ determined in the step (3) and with a graded time window, on the single event data sets acquired by the respective detector modules; and a fine estimated value $\Delta T_{fine}$ of the detection starting time difference of each detector module is determined. The step (4) includes steps (4.1)-(4.3).

In the step (4.1), the synchronization correction and a coincidence peak searching with the initial time window $TW_{ini}$ are performed, based on the obtained coarse estimated value $\Delta T_{crs}$ of the detection starting time difference, on each single event data set.

In the step (4.2), for each detector module, a center offset $\Delta T_i$ of an obtained statistical histogram of coincidence events is analyzed; in the case that the center offset $\Delta T_i$ meets a precision index requirement, an iteration is stopped, and the center offset $\Delta T_i$ of the obtained statistical histogram of the coincidence events is set as the fine estimated value $\Delta T_{fine}$ of the detection starting time difference of the detector module; otherwise, the time window is shortened with a minification of N, and the step (4.2) is repeated.

In the step (4.3), a weight accumulation is performed on the respective obtained center offsets $\Delta T_i$ to obtain the fine estimated value $\Delta T_{fine}$, here i is the number of iteration. Hence, the fine estimated value $\Delta T_{fine}$ of the detection starting time difference of each detector module may be determined with the following formula:

$$\Delta T_{fine} = \sum_{i=1}^{n} \Delta T_i.$$

In a graded time window approach in the step (4.2), graded coincidence time windows with various sizes are set, to gradually approximate a precision of the obtained statistical histogram of the coincidence events to the precision index. The precision index is a precision of a coincidence time resolution and is flexibly set based on application requirements.

In the step (5), the detection starting time difference of each detector module is determined based on the difference of coarse time and the difference of fine time obtained in the step (3) and the step (4), and the synchronization correction and a coincidence discrimination are performed on the single event data set obtained by each detector module, to obtain the coincidence events.

Figure 1A:
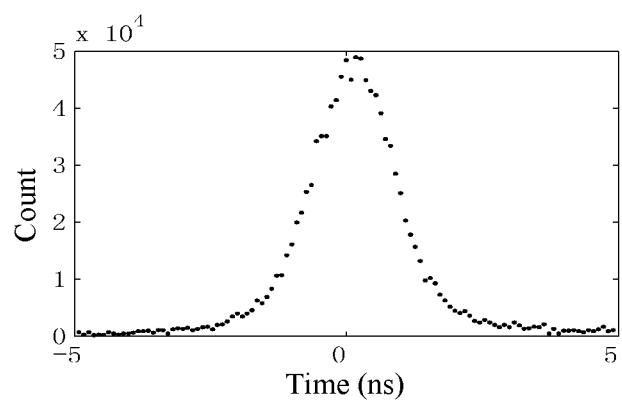
FIG. 1(a) is a statistical distribution chart of coincidence events obtained when adopting a synchronization signal.
Figure 1B:
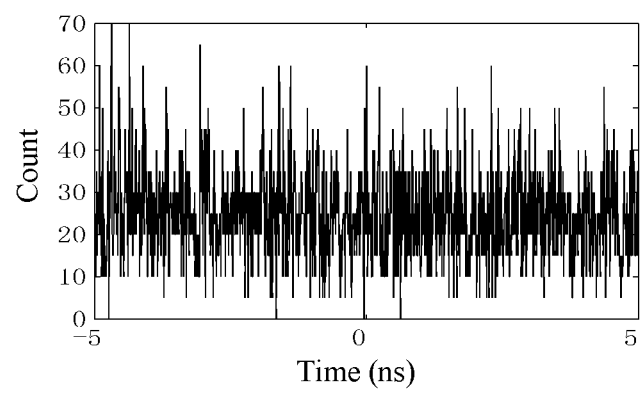
FIG. 1(b) is a statistical distribution chart of coincidence events obtained when not adopting a synchronization signal.

FIG. 1 shows an affect on coincidence event discrimination by adopting a synchronization signal in the method for synchronizing the list-mode data of the single events in the PET imaging provided in the disclosure. Where FIG. 1(a) is a statistical distribution chart of coincidence events obtained when adopting a synchronization signal, and FIG. 1(b) is a statistical distribution chart of coincidence events obtained when not adopting a synchronization signal.

Figure 6:
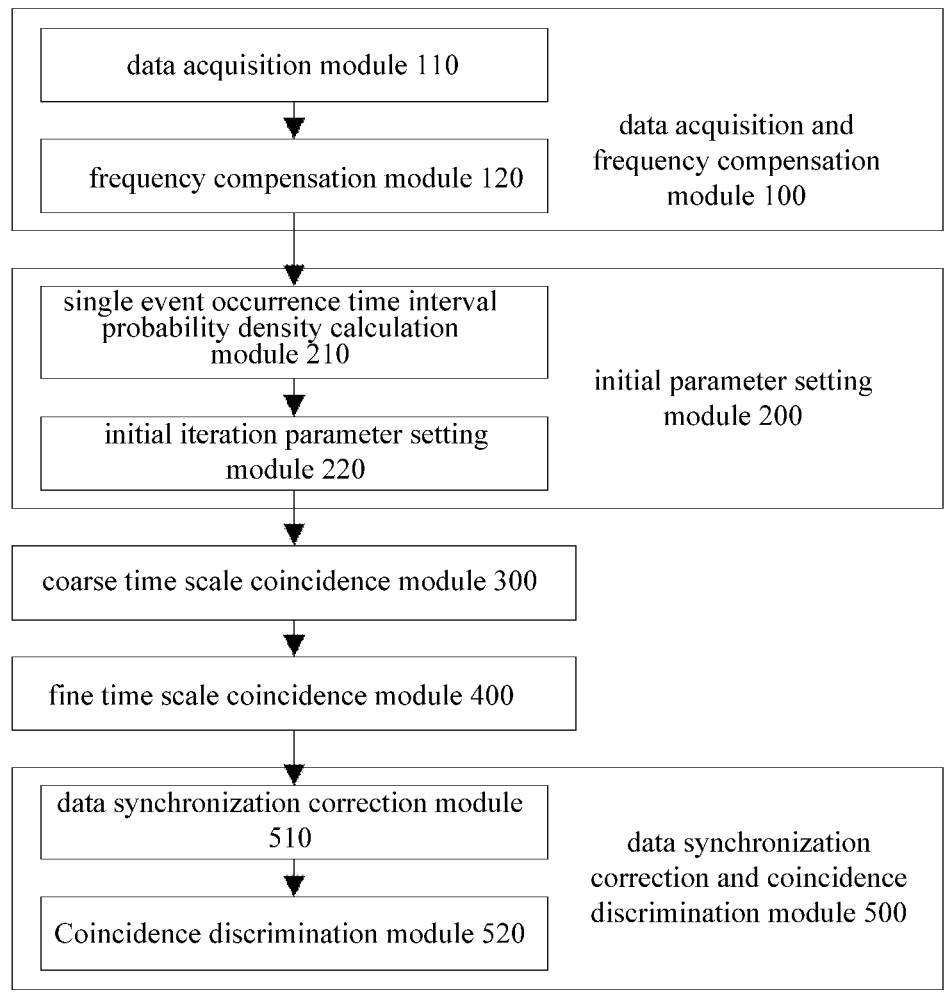
FIG. 6 is a structure diagram of a system for synchronizing list-mode data of single events in a PET imaging in the disclosure.

As shown in FIG. 6, a system for synchronizing list-mode data of single events in a PET imaging provided in the disclosure includes: a data acquisition and frequency compensation module 100, an initial parameter setting module 200, a coarse time scale coincidence module 300, a fine time scale coincidence module 400, and a data synchronization correction and coincidence discrimination module 500.

As shown in FIG. 6, the data acquisition and frequency compensation module 100 is for acquiring and storing list-mode data of single events of respective basic detector modules working with respective local reference clock sources, performing a frequency difference compensation on the single event data, and transferring corrected list-mode data of the single events to the initial parameter setting module 200. The data acquisition and frequency compensation module 100 includes two sub-modules: a data acquisition module 110 and a frequency compensation module 120. The data acquisition module 110 is for transferring the list-mode data of the single events including time information, energy information and position information of the single events, generated by the respective detector modules and sorted chronologically, to a computer and storing the list-mode data in the computer. The frequency compensation module 120 is for compensating frequency differences of the local reference clock sources used in the respective detector modules, and transferring the compensated list-mode data of the single events to the initial parameter setting module 200.

As shown in FIG. 6, the initial parameter setting module 200 sets initial parameters based on single event data sets corrected by the data acquisition and frequency compensation module 100. The initial parameter setting module 200 includes two sub-modules: a single event occurrence time interval probability density calculation module 210 and an initial iteration parameter setting module 220. The single event occurrence time interval probability density calculation module 210 is for calculating a probability density of time intervals between occurrences of single events in a single event data set in each detector module, and transferring the obtained probability density to the initial iteration parameter setting module 220 to set initial parameters. The single event occurrence time interval probability density calculation module 210 performs a backward difference on the single event data set in each detector module and performs a statistical analysis on obtained differential data, to obtain the probability density. The initial iteration parameter setting module 220 is for setting initial iteration parameters, and transferring obtained initial parameters to the coarse time scale coincidence module 300 and the fine time scale coincidence module 400. The initial parameters set by the initial iteration parameter setting module 220 include: initial iteration space parameter, initial time interval parameter and initial time window parameter.

Setting of the initial parameters includes the following steps (1)-(4).

In the step (1), the initial iteration space parameter is set.

A merge sort is performed on the single event data sets of the respective detector modules based on timestamps; a position M corresponding to a detection starting time instant $T_i$ of an i-th detector module is searched for in an obtained list; a single instant event time $T_{ci}$ of a position M-N in the obtained list is read, where N is number of consecutive events from an identical detector module, $N \in [1, M-1]$; and a probability of an occurrence of $T_{ci}$ is calculated with the following formula:

$$P_i < \int_{T_i - T_{ci}}^{+\infty} f_k(x) dx \cdot \int_{\frac{(T_i - T_{ci})}{N}}^{+\infty} f_i(x) dx.$$

Where k is the serial number of a detector module corresponding to a position 1 in the obtained list, and the initial iteration space parameter may be determined with the following formula:

$TR_{ini} = T_i - T_{ci}$, where $T_{ci}$ is the instant event time corresponding to the position M-N in the obtained list.

In the step (2), the initial time interval parameter is set.

An instant event time $T_k$ corresponding to the position 1 in the list obtained in step (2.1) is read, where the content of the step (2.1) may be referred to the foregoing description of the method. An initial value $\Delta T_{ini}$ of a difference between respective detection starting time instants of the i-th detector module and the k-th detector module is determined with the following formula:

$$\Delta T_{ini} = T_i - T_k + \frac{TR_{ini}}{2} \quad i \neq k$$
$$\Delta T_{ini} = 0 \quad i = k$$

In the step (3), the initial time window parameter is set.

The instant event time $T_k$ corresponding to the position 1 in the list obtained in step (2.2) is read, where the content of the step (2.2) may be referred to the foregoing description of the method. An initial coincidence time window $TW_{ini}$ of the i-th and the k-th detector modules is determined with the following formula:

$$TW_{ini} = TR_{ini}/L_i.$$

Where $L_i$ represents coefficient factors of time windows of the respective detector modules, And $L_i$ may be determined with the following formula:

$$L_i > 2 \cdot \frac{TR_{ini}}{E(TI_i) + E(TI_k)}.$$

Where $E(TI_k)$ is an expectation of time intervals of occurrences of events of the detector module k which transfers single event data first; $E(TI_i)$ is an expectation of time intervals of occurrences of events of detector module i requiring synchronization, and may be determined with the following formula:

$$E(TI_i) = \int_{-\infty}^{+\infty} x \cdot f_i(x) dx.$$

Figure 5A:
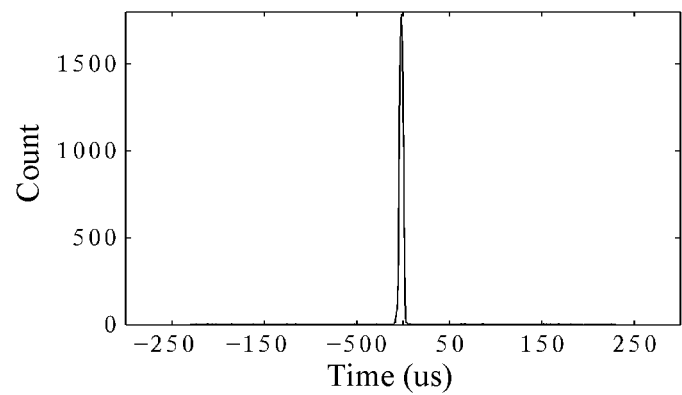
FIG. 5(a) is a statistical distribution chart of coincidence events, obtained with a coincidence time window of 250 ns.
Figure 5B:
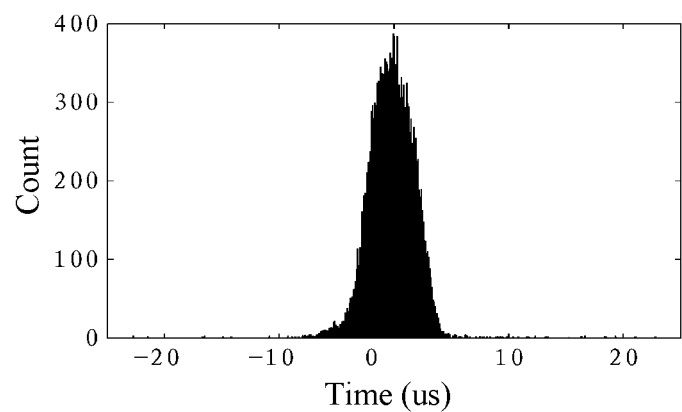
FIG. 5(b) is a statistical distribution chart of coincidence events, obtained with a coincidence time window of 25 ns.

FIG. 5 illustrates statistical distribution charts of the coincidence events, obtained through a fine time scale coincidence in the disclosure; where FIG. 5(a) is a statistical distribution chart of the coincidence events, obtained with a coincidence time window of 250 ns; and FIG. 5(b) is a statistical distribution chart of the coincidence events, obtained with a coincidence time window of 25 ns.

The coarse time scale coincidence module 300 is for obtaining a coarse estimated value of a detection starting time difference of each detector module; performing, based on the initial parameters set by the initial parameter setting module 200 and with an iterative peak searching, a synchronization correction and a coincidence peak searching on the single event set acquired by each detector module; and obtaining the coarse estimated value $\Delta T_{crs}$ of the detection starting time difference of each detector module through a coarse time scale coincidence. The coincidence peak searching in the coarse time scale coincidence module 300 is performed based on a statistical characteristic of the events in the PET imaging, and is implemented through the following steps (3.1), (3.2) and (3.3).

In the step (3.1), the synchronization correction and the coincidence peak searching of each single event data set are performed based on the initial parameters set in the step (2).

In the step (3.2), a coincidence result obtained in the step (3.1) is analyzed. For each detector module, in case that a peak in a statistical histogram of coincidence events may be obtained, an iteration is stopped. Otherwise, the time interval parameter $\Delta T_{ini}$ is adjusted to perform the coincidence peak searching and the step (3.2) is repeated.

In the step (3.3), a center offset $\Delta T_{offset}$ of a statistical histogram of the coincidence events, obtained in the step (3.2), is the coarse estimated value $\Delta T_{crs}$.

The fine time scale coincidence module 400 is for acquiring a fine estimated value of the detection starting time difference of each detector module; performing, based on the coarse estimated value obtained by the coarse time scale coincidence module 300 and with a graded time window, the synchronization correction and the coincidence peak searching on the single event data set obtained by each detector module; and determining a fine estimated value $\Delta T_{fine}$ of the detection starting time difference of each detector module. The fine time scale coincidence module 400 sets the graded time window, i.e., sets coincidence time windows with various sizes, to gradually approximate a precision of the obtained statistical histogram of the coincidence events to a precision index, and an implementation is described with the following steps (4.1)-(4.3).

In the step (4.1), the synchronization correction, and a coincidence peak searching with the initial time window $TW_{ini}$ are performed, based on the obtained coarse estimated value $\Delta T_{crs}$ of the detection starting time difference, on each single event data set.

In the step (4.2), the obtained center offset $\Delta T_i$ of the statistical histogram of the coincidence events is analyzed; in the case that the center offset $\Delta T_i$ meets a precision index requirement, an iteration is stopped; otherwise, the graded time window is used to perform the coincidence peak searching, and the step (4.2) is repeated.

In the step (4.3), a weight accumulation is performed on the respective obtained center offsets $DT_i$ to obtain the fine estimated value $\Delta T_{fine}$.

The data synchronization correction and coincidence discrimination module 500 is for performing a weight accumulation, based on the coarse estimated value and the fine estimated value of the detection starting time difference respectively obtained by the coarse time scale coincidence module 300 and the fine time scale coincidence module 400, to obtain the detection starting time difference of each basic detector module; and performing the synchronization correction and a coincidence event discrimination on a corresponding single event data set, to obtain the coincidence events.

The method for synchronizing the list-mode data of the single events in the PET imaging and the system thereof in the disclosure are further verified with data of a case below. Some parameters are involved, and the parameters are required to be adjusted based on specific processed data to achieve a good performance. The parameters of the processed data in the application case are listed below.

An initial value of the iteration space $TR_{ini}$ in the step (2.2) is set within [−5.851509300214e-04, 5.851509300214e-04] s.

An initial value of the time interval $\Delta T_{ini}$ in the step (2.3) is set as −24.330730944588 s.

An initial value of the time window $TW_{ini}$ in the step (2.4) is set as 2.500000000000e-05 s.

A value of N in the step (4.2) is set as 10.

Figure 7A:
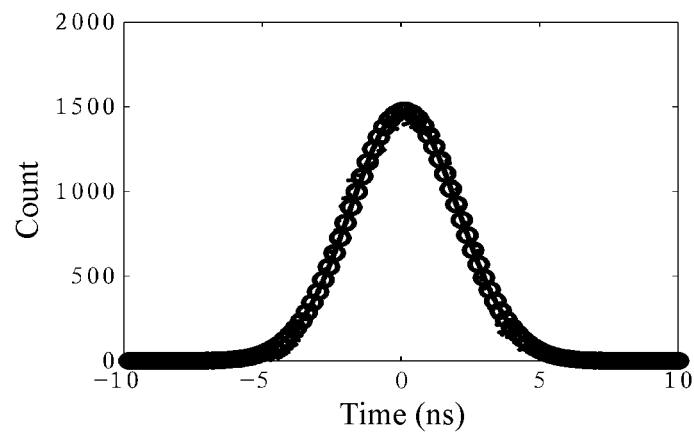
FIG. 7(a) is a statistical distribution chart of coincidence events, obtained through the disclosure.
Figure 7B:
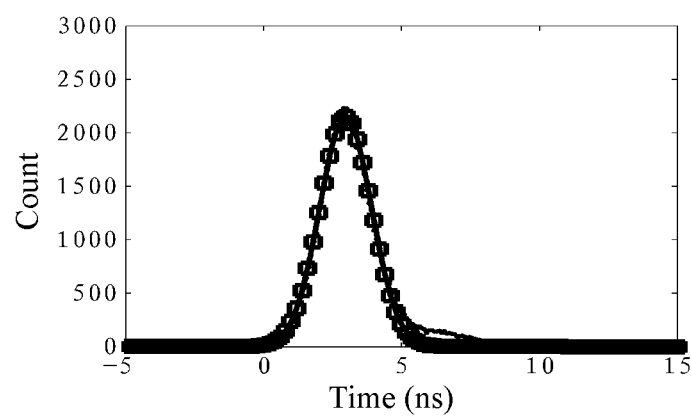
FIG. 7(b) is a statistical distribution chart of coincidence events, obtained by using a global clock.

FIG. 7 shows contrast results of a coincidence time resolution with the method provided in the disclosure, where FIG. 7(a) shows a time resolution obtained with the method provided in the disclosure, and FIG. 7(b) shows a time resolution obtained through a hardware global clock solution.

For those skilled in the art, obviously the disclosure is not limited to the details of the foregoing exemplary embodiments, and the disclosure may be achieved with other implementations without departing from the spirit or basic features of the disclosure. Therefore, the embodiments should be considered as exemplary and not limitative anyway, and the scope of the application should be defined by the appended claims rather than the foregoing description. Hence, the disclosure intends to include all modifications fall within the definitions and scopes of the equivalent of the appended claims. Any reference numeral in the appended claims should not be considered as limitation to concerning claims.

Further, it should be understood that, although the specification is described with embodiments, but not every embodiment includes only one independent technical solution. The description mode of the specification is merely for the sake of clarity. Those skilled in the art should take the specification as an entirety. The technical solutions in the embodiments may be combined to form other embodiments which can be understood by those skilled in the art.

What is claimed is:

1. A method for synchronizing list-mode data of single events in a Positron Emission Tomography (PET) imaging, comprising:
    step 1, acquiring and storing, by a computer, list-mode data of single events of each of a plurality of basic detector modules working with a local reference clock source, and performing, by a receiving device, a frequency difference compensation on a single event data set of the list-mode data of the single events based on a time difference between two synchronization requests of each of the plurality of basic detector modules;
    step 2, calculating, by the computer, a probability density of time intervals between occurrences of single events in the single event data set acquired by each of the plurality of basic detector modules, and setting, by the computer, initial parameters set, which comprises an initial iteration space parameter $TR_{ini}$, an initial time interval parameter $\Delta T_{ini}$ and an initial time window parameter $TW_{ini}$, based on the probability density of the time intervals between the occurrences of the single events in the single event data set;
    step 3, performing, by the computer, based on the initial parameters set in the step 2 and with an iterative peak searching, a first synchronization correction and a coincidence peak searching on the single event data set acquired by each of the plurality of basic detector modules; and determining, by the computer, a coarse estimated value of a detection starting time difference of each of the plurality of basic detector modules,
        wherein, the first synchronization correction comprises adjusting time instants at which the single events occur in each of the plurality of basic detector modules, based on a time interval parameter calculated by each of the plurality of basic detector modules,
        wherein the coincidence peak searching is performed based on a statistical characteristic of events in the PET imaging,
        wherein said events in the PET imaging comprise coincidence events and random events,
        wherein a statistical characteristic of the coincidence events is a Gaussian distribution, and a statistical characteristic of the random events is a uniform random distribution;
    step 4, performing, by the computer, based on the coarse estimated value of detection starting time difference obtained in the step 3 and with a graded time window, a second synchronization correction and a coincidence peak searching on the single event data set acquired by each of the plurality of basic detector modules; and determining a fine estimated value of the detection starting time difference of each of the plurality of basic detector modules;
    step 5, performing, by the computer, a weight accumulation on the coarse estimated value and the fine estimated value of the detection starting time difference, respectively obtained in the step 3 and the step 4, to determine the detection starting time difference of each of the plurality of basic detector modules; and performing, by the computer, a third synchronization correction and a coincidence event discrimination on the single event data set acquired by each of the plurality of basic detector modules, to obtain the coincidence events; and
    step 6, forming, by the computer, an image based on the coincidence events.

2. The method for synchronizing the list-mode data of the single events in the PET imaging according to claim 1, wherein in the step 1, each of the plurality of basic detector modules generates the list-mode data of the single events comprising time information, energy information and position information of the events, and the list-mode data of the single events are transferred to and stored in a computer.

3. The method for synchronizing the list-mode data of the single events in the PET imaging according to claim 1, wherein the frequency difference compensation in the step 1 comprises:
    periodically sending, by each of the plurality of basic detector modules, frequency synchronization requests in a data transmission channel based on a value of a counter in each of the plurality of basic detector modules;
    measuring, by a receiving device, a time difference between two synchronization requests of each of the plurality of basic detector modules; and
    generating, by the computer, a look-up table for frequency differences of each of the plurality of basic detector modules based on the respective time differences, to compensate, in real time, the frequency differences introduced by the local reference clock source.

4. The method for synchronizing the list-mode data of the single events in the PET imaging according to claim 1, wherein in the step 2, the probability density $f_i(x)$ of time intervals $TI_i$ between the occurrences of the single events in the single event data set acquired by each of the plurality of basic detector modules is obtained by, performing a backward difference on each single event data set and performing a statistical analysis on obtained differential data, where i represents serial numbers of each of the plurality of basic detector modules and x represents the time intervals of the occurrences of the single events.

5. The method for synchronizing the list-mode data of the single events in the PET imaging according to claim 4, wherein in the step 2, comprises:
    step 2.1 of initializing the iteration space parameter $TR_{ini}$, comprising:
    performing a merge sort on the single event data sets of each of the plurality of basic detector modules; searching for a position M corresponding to a detection starting time instant $T_i$ of an i-th basic detector module in an obtained list; reading an instant event time $T_{ci}$ corresponding to a position M-N in the list, where N is the number of consecutive events from an identical basic detector module, $N \in [1, M-1]$; and calculating a probability of an occurrence of $T_{ci}$ with a formula of:

$$P_i < \int_{T_i - T_{ci}}^{+\infty} f_k(x) dx \cdot \int_{\frac{(T_i - T_{ci})}{N}}^{+\infty} f_i(x) dx;$$

wherein k is a serial number of a basic detector module corresponding to a position 1 in the obtained list, and an initial value $TR_{ini}$ of the iteration space parameter is determined with a formula of:

$$TR_{ini} = T_i - T_{ci};$$

where $T_{ci}$ is the instant event time corresponding to the position M-N in the obtained list;

step 2.2 of initializing the time interval parameter $\Delta T_{ini}$, comprising:

reading an instant event time $T_k$ corresponding to the position 1 in the list obtained in the step 2.1, and determining an initial value $\Delta T_{ini}$ of a difference between detection starting time instants of the i-th basic detector module and the k-th basic detector module with a formula of:

$$\Delta T_{ini} = T_i - T_k + \frac{TR_{ini}}{2} \quad i \neq k$$
$$\Delta T_{ini} = 0 \quad i = k$$

step 2.3 of initializing the time window parameter $TW_{ini}$, comprising:

reading the instant event time $T_k$ corresponding to the position 1 in the list obtained in the step 2.1, and determining an initial value $TW_{ini}$ of a coincidence time window of the i-th and the k-th basic detector modules with a formula of:

$$TW_{ini} = TR_{ini}/L_i;$$

where $L_i$ represents coefficient factors of time windows of each of the plurality of basic detector modules, and $L_i$ is determined with a formula of:

$$L_i > 2 \cdot \frac{TR_{ini}}{E(TI_i) + E(TI_k)};$$

where $E(TI_k)$ is an expectation of time intervals of occurrences of events of each of the plurality of basic detector modules k which transfers single event data first, and $E(TI_i)$ is an expectation of time intervals of occurrences of events of each of the plurality of basic detector modules i requiring synchronization and is determined with a formula of:

$$E(TI_i) = \int_{-\infty}^{+\infty} x \cdot f_i(x) dx.$$

6. The method for synchronizing the list-mode data of the single events in the PET imaging according to claim 1, wherein in the step 3, the coarse estimated value $\Delta T_{crs}$ of the detection starting time difference of each of the plurality of basic detector modules is determined through a coarse time scale coincidence, and the step 3 comprises:

step 3.1, performing, based on the initial parameters set in the step 2, the first synchronization correction and the coincidence peak searching on the single event data set acquired by each of the plurality of basic detector modules;

step 3.2, analyzing a coincidence result obtained in the step 3.1; in the case that a peak in a statistical histogram of coincidence events is obtained, stopping an iteration; otherwise, adjusting the time interval parameter $\Delta T_{ini}$ to perform the coincidence peak searching and repeating the step 3.2; and step 3.3, setting, based on a center offset $\Delta T_{offset}$ of the statistical histogram of the coincidence events obtained in the step 3.2, the coarse estimated value $\Delta T_{crs}$ of the detection starting time difference of each of the plurality of basic detector modules.

7. The method for synchronizing the list-mode data of the single events in the PET imaging according to claim 6, wherein in the step 4, the fine estimated value $\Delta T_{fine}$ of the detection starting time difference of each of the plurality of basic detector modules is determined with a fine time scale coincidence, and the step 4 comprises:

step 4.1, performing, based on the coarse estimated value $\Delta T_{crs}$ of the detection starting time difference of each of the plurality of basic detector modules obtained in the step 3.2, the second synchronization correction, and a coincidence peak searching with the initial time window $TW_{ini}$ on the single event data set in each of the plurality of basic detector modules;

step 4.2, analyzing a center offset $\Delta T_i$ of an obtained statistical histogram of coincidence events; in the case that the center offset $\Delta T_i$ meets a precision index requirement, stop the iteration; otherwise, performing the coincidence peak searching with a graded time window and repeating the step 4.2; and step 4.3, performing a weight accumulation on the obtained center offset $DT_i$, to obtain the fine estimated value $\Delta T_{fine}$, where i is the number of iteration.

8. The method for synchronizing the list-mode data of the single events in the PET imaging according to claim 7, wherein in the step 4.2, setting the graded time window comprises: setting coincidence time windows with various sizes, to gradually approximate a precision of the obtained statistical histogram of the coincidence events to a precision index.

9. The method for synchronizing the list-mode data of the single events in the PET imaging according to claim 7, wherein the precision index is a precision of a resolution of coincidence time.

10. A system for synchronizing list-mode data of single events in a Positron Emission Tomography (PET) imaging, the system comprising a data acquisition and frequency compensation module, an initial parameter setting module, a coarse time scale coincidence module, a fine time scale coincidence module, and a data synchronization correction and coincidence discrimination module; wherein the data acquisition and frequency compensation module is configured to, acquire and store list-mode data of single events of each of a plurality of basic detector modules working with respective local reference clock sources, and perform a frequency difference compensation on the list-mode data of the single events based on a time difference between two synchronization requests of each of the plurality of basic detector modules;

the initial parameter setting module is configured to, calculate a probability density of time intervals between occurrences of single events in a single event data set acquired by each of the plurality of basic detector modules, and set initial parameters set comprising an initial iteration space parameter $TR_{ini}$, an initial time interval parameter $\Delta T_{ini}$ and an initial time window parameter $TW_{ini}$;

the coarse time scale coincidence module is configured to, obtain a coarse estimated value of a detection starting time difference of each of the plurality of basic detector modules;

the fine time scale coincidence module is configured to, obtain a fine estimated value of the detection starting time difference of each of the plurality of basic detector modules; and the data synchronization correction and coincidence discrimination module is configured to, determine the detection starting time difference of each of the plurality of basic detector modules, and perform a synchronization correction and a coincidence event discrimination on each single event data set, to obtain the coincidence events, wherein, the synchronization correction comprises adjusting time instants at which the single events occur in each of the plurality of basic detector modules, based on a time interval parameter calculated by each of the plurality of basic detector modules, wherein the coincidence peak searching is performed based on a statistical characteristic of events in the PET imaging, wherein said events in the PET imaging comprise coincidence events and random events, wherein a statistical characteristic of the coincidence events is a Gaussian distribution, and a statistical characteristic of the random events is a uniform random distribution, and wherein, an image is formed based on the coincidence events.

11. The system for synchronizing the list-mode data of the single events in the PET imaging according to claim 10, wherein the data acquisition and frequency compensation module comprises a data acquisition module and a frequency compensation module, the data acquisition module is configured to, transfer the list-mode data of the single events comprising time information, energy information and position information of the single events, generated by each of the plurality of basic detector modules and sorted chronologically, to a computer, and store the list-mode data in the computer; and the frequency compensation module is configured to, compensate frequency differences of the local reference clock sources used in each of the plurality of basic detector modules, and transfer the compensated list-mode data of the single events to the initial parameter setting module.

12. The system for synchronizing the list-mode data of the single events in the PET imaging according to claim 10, wherein the initial parameter setting module comprises a single event occurrence time interval probability density calculation module and an initial iteration parameter setting module, the single event occurrence time interval probability density calculation module is configured to, calculate the probability density of the time intervals between the occurrences of the single events in the single event data set in each of the plurality of basic detector modules; and the initial iteration parameter setting module is configured to, set the initial parameters, and transfer the initial parameters to the coarse time scale coincidence module and the fine time scale coincidence module.

13. The system for synchronizing the list-mode data of the single events in the PET imaging according to claim 12, wherein the single event occurrence time interval probability density calculation module performs a backward difference on the single event data set in each of the plurality of basic detector modules and performs a statistical analysis on obtained differential data.

14. The system for synchronizing the list-mode data of the single events in the PET imaging according to claim 10, wherein the coarse time scale coincidence module performs, based on the initial parameters set by the initial parameter setting module and with an iterative peak searching, first synchronization correction and a coincidence peak searching on the single event set acquired by each of the plurality of basic detector modules, to obtain the coarse estimated value of the detection starting time difference of each of the plurality of basic detector modules; wherein the coincidence peak searching is performed base on a statistical characteristic of events in the PET imaging.

15. The system for synchronizing the list-mode data of the single events in the PET imaging according to claim 10, wherein the fine time scale coincidence module performs, based on the coarse estimated value obtained by the coarse time scale coincidence module and with a graded time window, second synchronization correction and a coincidence peak searching on the single event data set obtained by each of the plurality of basic detector modules, to determine the fine estimated value of the detection starting time difference of each of the plurality of basic detector modules; wherein setting the graded time window comprises setting coincidence time windows with various sizes, to gradually approximate a precision of the obtained statistical histogram of the coincidence events to a precision index.

* * * * *

UNITED STATES PATENT AND TRADEMARK OFFICE
CERTIFICATE OF CORRECTION

PATENT NO. : 10,930,031 B2
APPLICATION NO. : 14/408935
DATED : February 23, 2021
INVENTOR(S) : Qingguo Xie Page 1 of 1

It is certified that error appears in the above-identified patent and that said Letters Patent is hereby corrected as shown below:

On the Title Page

On page 2, in Column 2, item (56), Other Publications, Line 6, delete "Nang," and insert --Wang,--.

In the Drawings

In sheet 3 of 6, FIG. 3, Line 1 X-axis, delete "(us)" and insert --(ns)--.

In sheet 3 of 6, FIG. 4, Line 1 X-axis, delete "(us)" and insert --(ns)--.

In sheet 4 of 6, FIG. 5a, Line 1 X-axis, delete "(us)" and insert --(ns)--.

In sheet 4 of 6, FIG. 5b, Line 1 X-axis, delete "(us)" and insert --(ns)--.

In the Specification

In Column 5, Line 38, delete "$DT_i$," and insert --$\Delta T_i$,--.

In Column 9, Line 41, delete "timeinstant" and insert --time instant--.

In Column 14, Line 34, delete "DT" and insert --$\Delta T_i$--.

In the Claims

In Column 18, Line 39, Claim 7, delete "$DT_i$," and insert --$\Delta T_i$,--.

Signed and Sealed this
Twenty-fifth Day of May, 2021

Drew Hirshfeld
*Performing the Functions and Duties of the*
*Under Secretary of Commerce for Intellectual Property and*
*Director of the United States Patent and Trademark Office*